United States Patent
Blackaby et al.

(10) Patent No.: US 7,226,926 B2
(45) Date of Patent: *Jun. 5, 2007

(54) 8-FLUOROIMIDAZO 1,2-A PYRIDINE DERIVATIVES AS LIGANDS FOR GABA RECEPTORS

(75) Inventors: Wesley Peter Blackaby, Buckhurst Hill (GB); Jose Luis Castro Pineiro, Bishops Stortford (GB); Simon Charles Goodacre, Benington (GB); David James Hallett, Watford (GB); Alexander Charles Humphries, Stevenage (GB); Philip Jones, Pomezia (IT); Kevin John Merchant, Ware (GB); Michael Reader, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 158 days.

This patent is subject to a terminal disclaimer.

(21) Appl. No.: 10/515,165

(22) PCT Filed: May 23, 2003

(86) PCT No.: PCT/GB03/02250

§ 371 (c)(1),
(2), (4) Date: Nov. 18, 2004

(87) PCT Pub. No.: WO03/099817

PCT Pub. Date: Dec. 4, 2003

(65) Prior Publication Data

US 2006/0052385 A1    Mar. 9, 2006

(30) Foreign Application Priority Data

May 24, 2002 (GB) .................................. 0212049.1

(51) Int. Cl.
*A61K 31/437* (2006.01)
*A61K 31/506* (2006.01)
*C07D 544/294* (2006.01)
*C07D 546/121* (2006.01)

(52) U.S. Cl. ..................... 514/256; 514/300; 544/294; 546/121

(58) Field of Classification Search ................ 546/121; 514/256, 300; 544/294
See application file for complete search history.

(56) References Cited

U.S. PATENT DOCUMENTS

| 6,642,229 | B2 * | 11/2003 | Blackaby et al. | 514/233.2 |
| 6,872,731 | B2 * | 3/2005 | Crawforth et al. | 514/300 |
| 7,030,128 | B2 * | 4/2006 | Blackaby et al. | 514/259.1 |
| 2005/0165048 | A1 * | 7/2005 | Goodacre et al. | 514/303 |

FOREIGN PATENT DOCUMENTS

| WO | WO01/38326 | | 11/2000 |
| WO | WO01/90108 | | 5/2001 |
| WO | WO02/076983 | | 3/2002 |
| WO | WO03/076442 | A1 * | 9/2003 |

OTHER PUBLICATIONS

Clayton et al., CAS Document No. 139:261331, Registry No. 603272-68-0.*
Kawamura et al., CAS Document No. 144:292780, Registry No. 878805-55-1.*
Accession No. 2003:737761, Registry No. 603272-68-0.*

* cited by examiner

*Primary Examiner*—Taofiq Solola
(74) *Attorney, Agent, or Firm*—J. Eric Thies; William Krovatin

(57) ABSTRACT

A class of 8-fluoroimidazo[1,2-α]pyridine derivatives, substituted at the 3-position by an optionally substituted five-membered or six-membered heteroaromatic ring, being selective ligands for $GABA_A$ receptors, in particular having high affinity for the α2 and/or α3 and/or α5 subunit thereof, are accordingly of benefit in the treatment and/or prevention of adverse conditions of the central nervous system, including anxiety, convulsions and cognitive disorders.

14 Claims, No Drawings

8-FLUOROIMIDAZO 1,2-A PYRIDINE DERIVATIVES AS LIGANDS FOR GABA RECEPTORS

CROSS REFERENCE TO RELATED APPLICATIONS

This application is a U.S. National Phase application under 35 U.S.C. § 371 of PCT Application No. PCT/GB03/02250, filed May 23, 2003, which claims priority under 35 U.S.C. § 119 from GB Application No. 0212049.1, filed May 24, 2002.

The present invention relates to a class of substituted imidazo-pyridine derivatives and to their use in therapy. More particularly, this invention is concerned with 8-fluoroimidazo[1,2-α]pyridine analogues which are substituted in the 3-position by an optionally substituted heteroaromatic ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxyolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

WO 01/38326 describes a class of 3-phenylimidazo[1,2-α]pyridine derivatives which are stated to be selective ligands for $GABA_A$ receptors, in particular having high affinity for the α2 and/or α3 subunit thereof, and accordingly to be of benefit in the treatment and/or prevention of neurological disorders, including anxiety and convulsions. However, there is no disclosure nor any suggestion in that publication of: (i) substitution with a fluorine atom at the 8-position of the imidazo[1,2-α]pyridine nucleus; or (ii) replacement of the substituted phenyl moiety at the 3-position with an optionally substituted heteroaromatic ring.

The present invention provides a class of imidazo-pyridine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

Moreover, the compounds according to the present invention possess remarkable receptor occupancy at low doses, and interesting pharmacokinetic properties, notably in terms of improved oral bioavailability and enhanced metabolic stability.

The present invention provides a compound of formula I, or a salt or prodrug thereof:

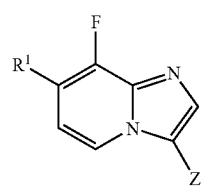

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

$R^1$ represents hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$; and $R^a$ and $R^b$ independently represent hydrogen, hydrocarbon or a heterocyclic group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z.

Where Z in the compounds of formula I above represents a six-membered heteroaromatic ring, this ring may be optionally substituted by one or more substituents, typically by one or two substituents.

Suitably, the group Z is unsubstituted or monosubstituted.

Examples of optional substituents on the five-membered or six-membered heteroaromatic ring as specified for Z include halogen, cyano, trifluoromethyl, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, $C_{3-7}$ cycloalkyl, $C_{3-7}$ heterocycloalkyl, benzyl-tetrahydropyridinyl, oxy, hydroxy, $C_{1-6}$ alkoxy, methyltriazolyl($C_{1-6}$)alkoxy, $C_{1-6}$ alkylthio, $C_{1-6}$ alkylsulphonyl, $C_{2-6}$ alkylcarbonyl, amino, $C_{1-6}$ alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, (aminocarbonyl)(fluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, ($C_{2-6}$)alkylcarbonyl-phenyl, trifluorothio-phenyl, ($C_{1-6}$)alkylsulphonyl-phenyl, di($C_{1-6}$)alkylaminocarbonyl-phenyl, di($C_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl and optionally substituted heteroaryl, the optional substituents on the heteroaryl moiety being typically selected from oxy, halogen, cyano and $C_{1-6}$ alkyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The present invention includes within its scope tautomers of the compounds of formula I as defined above. For example, where Z represents an optionally substituted 2-hydroxypyridine moiety, this may co-exist, in whole or in part, with the corresponding 2-pyridone tautomer. It is to be understood that all such tautomers and mixtures thereof in any proportion are encompassed within the scope of the present invention.

Where the group Z represents an optionally substituted five-membered heteroaromatic ring, this is suitably a thiophene, thiazole or thiadiazole ring, either of which may be optionally substituted by one or, where possible, two substituents.

Where the group Z represents an optionally substituted six-membered heteroaromatic ring, this is suitably a pyridinyl or pyrimidinyl ring, either of which may be optionally substituted by one or more substituents, typically by one or two substituents. In one embodiment, Z represents monosubstituted pyridinyl. In another embodiment, Z represents monosubstituted pyrimidinyl.

Illustrative examples of optional substituents on the group Z include fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, oxy, hydroxy, methoxy, ethoxy, isopropoxy, tert-butoxy, methyltriazolylmethoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminosulphonyl-phenyl, dimethylaminocarbonyl-phenyl, (fluoro)(morpholinylmethyl)phenyl, (fluoro)(pyridinyl) phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl. Additionally, the group Z may be optionally substituted by (aminocarbonyl)(fluoro)phenyl.

Representative examples of optional substituents on the group Z include fluoro, trifluoromethyl, fluorophenyl, chlorophenyl, difluorophenyl, dichlorophenyl, (chloro)(fluoro)phenyl, cyanophenyl, (cyano)(fluoro)phenyl and (aminocarbonyl)(fluoro)phenyl.

One typical substituent which may be attached to the group Z is trifluoromethyl. Another typical substituent which may be attached to the group Z is (cyano)(fluoro)phenyl. An additional typical substituent which may be attached to the group Z is difluorophenyl.

In one embodiment, Z represents trifluoromethyl-pyridinyl.

In another embodiment, Z represents trifluoromethyl-pyrimidinyl.

In an additional embodiment, Z represents (cyano)(fluoro)phenyl-pyridinyl.

In a further embodiment, Z represents difluorophenyl-pyrimidinyl.

Additional embodiments of Z include fluorophenyl-pyridinyl, (aminocarbonyl)(fluoro)phenyl-pyridinyl, [(cyano)(fluoro)phenyl]-fluoropyridinyl, fluorophenyl-pyrimidinyl, chlorophenyl-pyrimidinyl, dichlorophenyl-pyrimidinyl, (chloro)(fluoro)phenyl-pyrimidinyl, cyanophenyl-pyrimidinyl and (aminocarbonyl)(fluoro)phenyl-pyrimidinyl.

Typically, $R^1$ represents hydrogen, hydrocarbon, a heterocyclic group, halogen, cyano, trifluoromethyl, —$OR^a$, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Representative values of $R^1$ include hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl and —$CR^a$=$NOR^b$, in which $R^a$ and $R^b$ are as defined above.

Itemised values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), cyanopropyl (especially 2-cyanoprop-2-yl), tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl.

Individual values of $R^1$ include hydrogen, hydroxypropyl (especially 2-hydroxyprop-2-yl), fluoropropyl (especially 2-fluoroprop-2-yl) and trifluoromethyl.

A favoured value of $R^1$ is 2-hydroxyprop-2-yl.

A particular value of $R^1$ is trifluoromethyl.

Another value of $R^1$ is hydrogen.

Suitably, $R^2$ is hydrogen.

Suitably, $R^3$ represents hydrogen or dimethylaminoethyl, especially hydrogen.

A particular sub-class of compounds according to the invention is represented by the compounds of formula IA, and salts and prodrugs thereof:

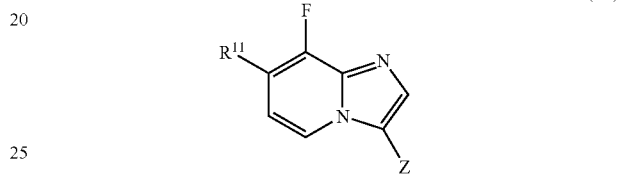

(IA)

wherein

Z is as defined above;

$R^{11}$ represents hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alkylamino($C_{1-6}$)alkyl.

Suitably, $R^4$ represents hydrogen or methyl, especially hydrogen.

Suitably, $R^5$ represents hydrogen, methyl, ethyl, hydroxyethyl or dimethylaminoethyl. Particular values of $R^5$ include hydrogen, hydroxyethyl and dimethylaminoethyl. Typically, $R^5$ represents hydrogen or dimethylaminoethyl, especially hydrogen.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Itemised values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), cyanopropyl (especially 2-cyanoprop-2-yl), tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ and $R^3$ are as defined above.

Representative values of R¹¹ include hydrogen, hydroxypropyl (especially 2-hydroxyprop-2-yl), fluoropropyl (especially 2-fluoroprop-2-yl) and trifluoromethyl.

A favoured value of R¹¹ is 2-hydroxyprop-2-yl.

A particular value of R¹¹ is trifluoromethyl.

Another value of R¹¹ is hydrogen.

One representative subset of the compounds of formula IA above is represented by the compounds of formula IIA, and salts and prodrugs thereof:

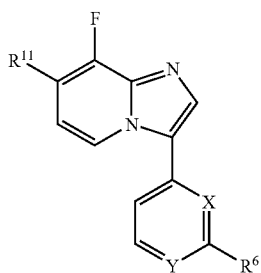

(IIA)

wherein

X represents CH or CF and Y represents N; or

X represents N and Y represents CH, CF or N;

R⁶ represents hydrogen, halogen, cyano, trifluoromethyl, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, C$_{3-7}$ cycloalkyl, C$_{3-7}$ heterocycloalkyl, benzyl-tetrahydropyridinyl, C$_{1-6}$ alkoxy, methyltriazolyl(C$_{1-6}$)alkoxy, C$_{1-6}$ alkylthio, C$_{1-6}$ alkylsulphonyl, C$_{2-6}$ alkylcarbonyl, amino, C$_{1-6}$ alkylamino, di(C$_{1-6}$)alkylamino, C$_{2-6}$ alkylcarbonylamino, phenyl, (C$_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$)alkylcarbonyl-phenyl, trifluorothio-phenyl, (C$_{1-6}$)alkylsulphonyl-phenyl, di(C$_{1-6}$)alkylaminocarbonyl-phenyl, di(C$_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl or optionally substituted heteroaryl, the optional substituents on the heteroaryl moiety being selected from oxy, halogen, cyano and C$_{1-6}$ alkyl; and R¹¹ is as defined above.

The present invention suitably provides a compound of formula IIA as depicted above, or a salt or prodrug thereof, wherein X represents CH and Y represents N; or X represents N and Y represents CH or N; and R⁶ and R¹¹ are as defined above.

Illustrative values of R⁶ include hydrogen, fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, methoxy, ethoxy, isopropoxy, tert-butoxy, methyltriazolyl-methoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Representative values of R⁶ include trifluoromethyl, fluorophenyl, chlorophenyl, difluorophenyl, dichlorophenyl, (chloro)(fluoro)phenyl, cyanophenyl and (cyano)(fluoro)phenyl.

In one embodiment, R⁶ represents trifluoromethyl. In another embodiment, R⁶ represents (cyano)(fluoro)phenyl. In an additional embodiment, R⁶ represents difluorophenyl.

An illustrative subset of the compounds of formula IIA above is represented by the compounds of formula IIB, and salts and prodrugs thereof:

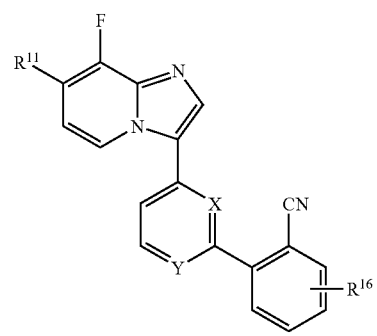

(IIB)

wherein X, Y and R¹¹ are as defined above; and

R¹⁶ represents hydrogen or fluoro.

In one embodiment, R¹⁶ represents hydrogen.

In another embodiment, R¹⁶ represents fluoro, in which case the fluorine atom R¹⁶ is favourably attached to the phenyl ring at the 4-, 5- or 6-position (relative to the cyano group at position 2).

In one embodiment of the compounds of formula IIA and IIB, X is CH and Y is N.

In another embodiment of the compounds of formula IIA and IIB, X is N and Y is CH.

In a further embodiment of the compounds of formula IIA and IIB, X and Y are both N.

In a still further embodiment of the compounds of formula IIA and IIB, X is CF and Y is N.

In an additional embodiment of the compounds of formula IIA and IIB, X is N and Y is CF.

Specific compounds within the scope of the present invention include:

8-fluoro-3-(6-trifluoromethylpyridin-2-yl)imidazo[1,2-α]pyridine;
8-fluoro-3-(2-trifluoromethylpyrimidin-4-yl)imidazo[1,2-α]pyridine;
2-[8-fluoro-3-(2-trifluoromethylpyrimidin-4-yl)imidazo[1,2-α]pyridin-7-yl]propan-2-ol;
4-fluoro-2-{6-[8-fluoro-7-(1-hydroxy-1-methylethyl)imidazo[1,2-α]pyridin-3-yl]pyridin-2-yl}benzonitrile;
5-fluoro-2-{6-[8-fluoro-7-(1-hydroxy-1-methylethyl)imidazo[1,2-α]pyridin-3-yl]pyridin-2-yl}benzonitrile;
3-fluoro-2-{6-[8-fluoro-7-(1-hydroxy-1-methylethyl)imidazo[1,2-α]pyridin-3-yl]pyridin-2-yl}benzonitrile;
2-{3-[2-(3,4-difluorophenyl)pyrimidin-4-yl]-8-fluoroimidazo[1,2-α]pyridin-7-yl}propan-2-ol;
2-{3-[2-(2,3-difluorophenyl)pyrimidin-4-yl]-8-fluoroimidazo[1,2-α]pyridin-7-yl}propan-2-ol;
2-{3-[2-(2,4-difluorophenyl)pyrimidin-4-yl]-8-fluoroimidazo[1,2-α]pyridin-7-yl}propan-2-ol;
2-{8-fluoro-3-[2-(3-fluorophenyl)pyrimidin-4-yl]imidazo[1,2-α]pyridin-7-yl}propan-2-ol;
2-{3-[2-(4-chloro-3-fluorophenyl)pyrimidin-4-yl]-8-fluoroimidazo[1,2-α]pyridin-7-yl}propan-2-ol;
2-{3-[2-(3-chloro-6-fluorophenyl)pyrimidin-4-yl]-8-fluoroimidazo[1,2-α]pyridin-7-yl}propan-2-ol;
2-{3-[2-(3-chloro-2-fluorophenyl)pyrimidin-4-yl]-8-fluoroimidazo[1,2-α]pyridin-7-yl}propan-2-ol;
2-{3-[2-(3-chloro-4-fluorophenyl)pyrimidin-4-yl]-8-fluoroimidazo[1,2-α]pyridin-7-yl}propan-2-ol;
2-{3-[2-(4-chlorophenyl)pyrimidin-4-yl]-8-fluoroimidazo[1,2-α]pyridin-7-yl}propan-2-ol;
2-{3-[2-(2,4-dichlorophenyl)pyrimidin-4-yl]-8-fluoroimidazo[1,2-α]pyridin-7-yl}propan-2-ol;
4-{4-[8-fluoro-7-(2-hydroxyprop-2-yl)imidazo[1,2-α]pyridin-3-yl]pyrimidin-2-yl}benzonitrile;
3-{4-[8-fluoro-7-(2-hydroxyprop-2-yl)imidazo[1,2-α]pyridin-3-yl]pyrimidin-2-yl}benzonitrile;
6-fluoro-3-{4-[8-fluoro-7-(2-hydroxyprop-2-yl)imidazo[1,2-α]pyridin-3-yl]pyrimidin-2-yl}benzonitrile;
2-fluoro-4-{4-[8-fluoro-7-(2-hydroxyprop-2-yl)imidazo[1,2-α]pyridin-3-yl]pyrimidin-2-yl}benzonitrile;
5-fluoro-2-{4-[8-fluoro-7-(2-hydroxyprop-2-yl)imidazo[1,2-α]pyridin-3-yl]pyrimidin-2-yl}benzonitrile;
5-fluoro-2-{4-[8-fluoro-7-(2-hydroxyprop-2-yl)imidazo[1,2-α]pyridin-3-yl]pyrimidin-2-yl}benzamide;
5-fluoro-2-{3-fluoro-6-[8-fluoro-7-(2-hydroxyprop-2-yl)imidazo[1,2-α]pyridin-3-yl]pyridin-2-yl}benzonitrile;
4-fluoro-2-{3-fluoro-6-[8-fluoro-7-(2-hydroxyprop-2-yl)imidazo[1,2-α]pyridin-3-yl]pyridin-2-yl}benzonitrile;
4-fluoro-2-{3-fluoro-4-[8-fluoro-7-(2-hydroxyprop-2-yl)imidazo[1,2-α]pyridin-3-yl]pyridin-2-yl}benzonitrile;
5-fluoro-2-{3-fluoro-4-[8-fluoro-7-(2-hydroxyprop-2-yl)imidazo[1,2-α]pyridin-3-yl]pyridin-2-yl}benzonitrile;
5-fluoro-2-{4-[8-fluoro-7-(2-hydroxyprop-2-yl)imidazo[1,2-α]pyridin-3-yl]pyridin-2-yl}benzonitrile;
2-{8-fluoro-3-[2-(3-fluorophenyl)pyrimidin-4-yl]imidazo[1,2-α]pyridin-7-yl}propan-2-ol;
3-fluoro-2-{4-[8-fluoro-7-(2-hydroxyprop-2-yl)imidazo[1,2-α]pyridin-3-yl]pyridin-2-yl}benzamide;
5-fluoro-2-{5-[8-fluoro-7-(2-hydroxyprop-2-yl)imidazo[1,2-α]pyridin-3-yl]pyridin-3-yl}benzonitrile;
5-fluoro-2-[3-fluoro-6-(8-fluoro-7-trifluoromethylimidazo[1,2-α]pyridin-3-yl)pyridin-2-yl]benzonitrile;
5-fluoro-2-[3-fluoro-4-(8-fluoro-7-trifluoromethylimidazo[1,2-α]pyridin-3-yl)pyridin-2-yl]benzonitrile;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and al subunits of the human $GABA_A$ receptor can conveniently be measured by procedures analogous to the protocol described in Wafford et al., *Mol. Pharmacol.*, 1996, 50, 670-678. The procedure will suitably be carried out utilising cultures of stably transfected eukaryotic cells, typically of stably transfected mouse Ltk-fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109-117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206-213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492-501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101-108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

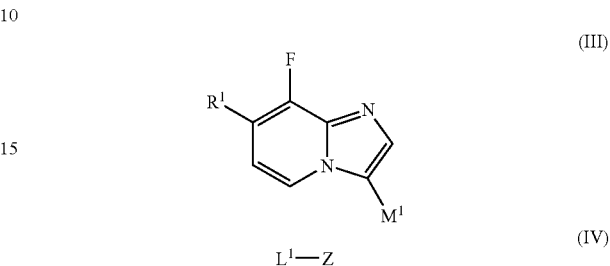

wherein Z and $R^1$ are as defined above, $L^1$ represents a suitable leaving group, and $M^1$ represents a boronic acid moiety —B(OH)$_2$ or a cyclic ester thereof formed with an organic diol, e.g. pinacol, 1,3-propanediol or neopentyl glycol, or $M^1$ represents —Sn(Alk)$_3$ in which Alk represents a $C_{1-6}$ alkyl group, typically n-butyl; in the presence of a transition metal catalyst.

The leaving group $L^1$ is typically a halogen atom, e.g. bromo or chloro.

The transition metal catalyst of use in the reaction between compounds III and IV is suitably tetrakis(triphenylphosphine)-palladium(0). The reaction is conveniently carried out at an elevated temperature in a solvent such as tetrahydrofuran, 1,4-dioxane or N,N-dimethylacetamide, typically in the presence of potassium phosphate, sodium carbonate, cesium carbonate or copper(I) iodide.

In an alternative procedure, the compounds according to the present invention may be prepared by a process which comprises reacting a compound of formula V with a compound of formula VI:

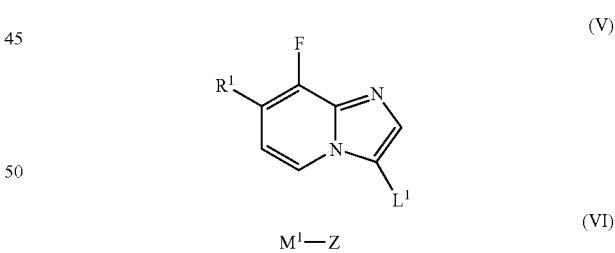

wherein Z, $R^1$, $L^1$ and $M^1$ are as defined above; in the presence of a transition metal catalyst; under conditions analogous to those described above for the reaction between compounds III and IV.

Where $M^1$ in the intermediates of formula III above represents —Sn(Alk)$_3$ in which Alk is n-butyl, this compound may be prepared by reacting a compound of formula V as defined above with tributyltin chloride.

The reaction is conveniently effected by stirring compound V with isopropylmagnesium chloride in a solvent such as tetrahydrofuran, with subsequent addition of tributyltin chloride.

Where $L^1$ in the intermediates of formula V above represents bromo, this compound may be prepared by bromination of the corresponding compound of formula VII:

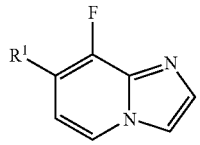

(VII)

wherein $R^1$ is as defined above; typically by treatment with bromine in methanol, in the presence of sodium acetate and optionally also potassium bromide.

The intermediates of formula VII may be prepared by reacting chloroacetaldehyde or bromoacetaldehyde, or an acetal derivative thereof, e.g. the dimethyl or diethyl acetal thereof, with the requisite compound of formula VIII:

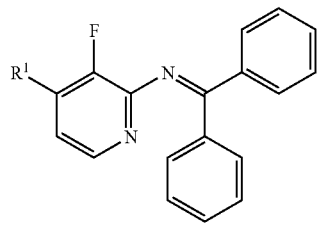

(VIII)

wherein $R^1$ is as defined above.

Where chloroacetaldehyde or bromoacetaldehyde is utilised as one of the reactants, the reaction is conveniently carried out by heating the reactants under basic conditions in a suitable solvent, e.g. sodium methoxide or sodium hydrogencarbonate in a lower alkanol such as methanol, ethanol or isopropanol. Where an acetal derivative of chloroacetaldehyde or bromoacetaldehyde, e.g. the dimethyl or diethyl acetal thereof, is utilised as one of the reactants, the reaction is conveniently effected by heating the reactants under acidic conditions, e.g. in aqueous hydrobromic acid.

The intermediates of formula VIII may be prepared by reacting benzophenone imine with a compound of formula IX:

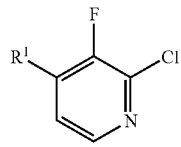

(IX)

wherein $R^1$ is as defined above.

The reaction is conveniently accomplished by heating in a solvent such as toluene, advantageously in the presence of a base such as cesium carbonate or sodium tert-butoxide, a transition metal catalyst such as palladium(II) acetate or tris(dibenzylideneacetone)dipalladium(0), and 2,2'-bis(diphenylphosphino)-1,1'-binaphthyl (BINAP).

In another procedure, the compounds according to the present invention wherein $R^1$ represents an aryl or heteroaryl moiety may be prepared by a process which comprises reacting a compound of formula X with a compound of formula XI:

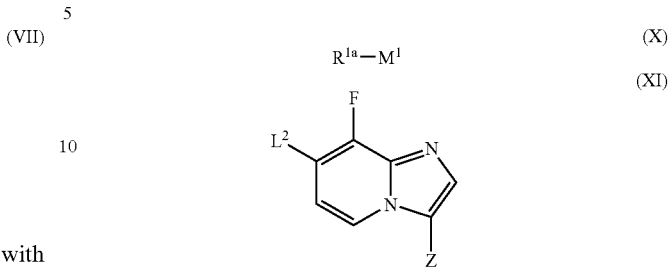

(X)

(XI)

wherein Z and $M^1$ are as defined above, $R^{1a}$ represents an aryl or heteroaryl moiety, and $L^2$ represents a suitable leaving group; in the presence of a transition metal catalyst.

The leaving group $L^2$ is typically a halogen atom, e.g. chloro.

The transition metal catalyst of use in the reaction between compounds X and XI is suitably tetrakis(triphenylphosphine)-palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)palladium(0), in which case the reaction is conveniently effected at an elevated temperature in a solvent such as 1,4-dioxane, typically in the presence of tri-tert-butylphosphine and cesium carbonate.

Where $L^2$ in the compounds of formula XI above represents a halogen atom, these compounds correspond to compounds of formula I as defined above wherein $R^1$ represents halogen, and they may therefore be prepared by any of the methods described above for the preparation of the compounds according to the invention.

In a further procedure, the compounds according to the invention may be prepared by a process which comprises reacting a compound of formula IV as defined above with a compound of formula VII as defined above in the presence of a transition metal catalyst.

The transition metal catalyst of use in the reaction between compounds IV and VII is suitably palladium(II) acetate, in which case the reaction is conveniently effected at an elevated temperature in the presence of triphenylphosphine in a solvent such as N,N-dimethylacetamide, typically in the presence of potassium acetate. Alternatively, the transition metal catalyst of use in the reaction between compounds IV and VII may suitably be tetrakis(triphenylphosphine)-palladium(0), in which case the reaction is conveniently effected at an elevated temperature in a solvent such as 1,4-dioxane, typically in the presence of cesium carbonate.

Where they are not commercially available, the starting materials of formula IV, VI, IX and X may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein the moiety Z is substituted by a halogen atom, e.g.

chloro or bromo, may be converted into the corresponding compound wherein the moiety Z is substituted by an aryl or heteroaryl group, e.g. 3,4-difluorophenyl, 2-cyanophenyl, 2-cyano-6-fluorophenyl or pyridin-3-yl, by treatment with the requisite aryl or heteroaryl boronic acid or cyclic ester thereof formed with an organic diol, e.g. 3,4-difluorophenylboronic acid, 2-cyanophenylboronic acid, 3-fluoro-2-(4,4,5,5-tetramethyl-[1,3,2]dioxaborolan-2-yl)benzonitrile or pyridine-3-boronic acid-1,3-propanediol cyclic ester, in the presence of a transition metal catalyst such as tetrakis(triphenylphosphine)palladium(0), in which case the reaction is conveniently effected at an elevated temperature in a solvent such as N,N-dimethylacetamide, aqueous 1,2-dimethoxyethane, aqueous 1,4-dioxane or aqueous tetrahydrofuran, typically in the presence of potassium phosphate, sodium carbonate or cesium carbonate; or by treatment with the appropriate stannyl reagent, e.g. 2-tributylstannylbenzonitrile, in the presence of a transition metal catalyst such as dichloro[1,1'-bis(diphenylphosphino)ferrocene]palladium(II), in which case the reaction is conveniently effected at a elevated temperature in a solvent such as N,N-dimethylacetamide, typically in the presence of lithium chloride and copper(I) chloride; or by treatment with the appropriate stannyl reagent in the presence of a transition metal catalyst such as tetrakis(triphenylphosphine)palladium(0), in which case the reaction is conveniently accomplished at an elevated temperature in a solvent such as tetrahydrofuran or 1,4-dioxane, typically in the presence of copper(I) iodide; or, where the moiety Z in the desired compound of formula I is substituted by imidazol-1-yl, simply by treatment with imidazole in the presence of a strong base such as lithium hexamethyldisilazide (LiHMDS). A compound of formula I wherein the moiety Z is substituted by pyridinyl may be converted into the corresponding compound wherein Z is substituted by N-oxypyridinyl by treatment with meta-chloroperbenzoic acid. A compound of formula I wherein Z is substituted by a halogen atom, e.g. iodo, may be converted, by treatment with isopropylmagnesium chloride, into a Grignard reagent which may be reacted with an aldehyde such as acetaldehyde to afford a secondary alcohol, e.g. the 1-hydroxyethyl derivative; and this compound may in turn be treated with an oxidising agent, e.g. Dess-Martin periodinane, to afford the corresponding compound of formula I wherein Z is substituted by acetyl. The resulting acetyl derivative may be converted, by treatment with methylmagnesium chloride, into the corresponding compound wherein Z is substituted by 2-hydroxyprop-2-yl; and this compound may in turn be treated with (diethylamino)sulfur trifluoride (DAST) to afford the corresponding compound of formula I wherein Z is substituted by 2-fluoroprop-2-yl. A compound of formula I wherein $R^1$ represents —C(O-Alk$^1$)$_2R^a$ initially obtained, wherein Alk$^1$ represents $C_{1-6}$ alkyl, typically methyl or ethyl, may be converted into the corresponding compound of formula I wherein $R^1$ represents —COR$^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula $H_2N$—OR$^b$ to provide a compound of formula I wherein $R^1$ represents —CH═NOR$^b$. Furthermore, a compound of formula I wherein $R^1$ represents —CH═NOH may be treated with triethylamine in the presence of 1,1'-carbonyldiimidazole to afford a corresponding compound of formula I wherein $R^1$ represents cyano. Alternatively, the compound of formula I wherein $R^1$ represents formyl may be reacted with a Grignard reagent of formula $R^a$MgBr to afford a compound of formula I wherein $R^1$ represents —CH(OH)R$^a$, and this compound may in turn be oxidised using manganese dioxide to the corresponding compound of formula I wherein $R^1$ represents —COR$^a$. The latter compound may then be condensed with a hydroxylamine derivative of formula $H_2N$—OR$^b$ to provide a compound of formula I wherein $R^1$ represents —CR$^a$═NOR$^b$. A compound of formula I wherein $R^1$ represents —CH(OH)R$^a$ may be converted into the corresponding compound of formula I wherein $R^1$ represents —CHFR$^a$ by treatment with DAST. Similarly, a compound of formula I wherein $R^1$ represents —COR$^a$ may be converted into the corresponding compound of formula I wherein $R^1$ represents —CF$_2$R$^a$ by treatment with DAST. A compound of formula I wherein $R^1$ represents amino may be converted into the corresponding compound of formula I wherein $R^1$ represents chloro by diazotisation, using sodium nitrite, followed by treatment with copper(I) chloride. A compound of formula I wherein $R^1$ represents —COCH$_3$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (p-tolylsulfonyl)methyl isocyanide (TosMIC) in the presence of potassium carbonate to afford the corresponding compound of formula I wherein $R^1$ represents oxazol-5-yl. A compound of formula I wherein $R^1$ represents hydroxymethyl may be treated with carbon tetrabromide and triphenylphosphine to afford the corresponding compound of formula I wherein $R^1$ represents bromomethyl, which may then be reacted (typically in situ) with the sodium salt of imidazole or 1H-[1,2,4]triazole to provide a compound of formula I wherein $R^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk-cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000-4000 dpm for total counts and less than 200 dpm for non-specific binding if using liquid scintillation counting, or 1500-2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [$^3$H]-flumazenil from the α2 and/or α3 and/or α5 subunit of the human GABA$_A$ receptor of 100 nM or less.

EXAMPLE 1

8-Fluoro-3-(6-trifluoromethylpyridin-2-yl)imidazo [1,2-α]pyridine n-Butyllithium (2.5 M in hexanes; 230 ml, 0.57 mol) was added to a solution of 1,4-diazabicyclo[2.2.2]octane (pre-dried by azeotropic removal of water with toluene) (63.8 g, 0.57 mol) in Et$_2$O (2.5 l) holding the temperature between −20 and −30° C. After stirring for 1 h, the temperature was adjusted to −65° C. and a solution of 3-fluoropyridine (50.0 g, 0.52 mol) in Et$_2$O (250 ml) was added dropwise over 10 min and the mixture stirred for a further 1 h. A solution of hexachloroethane (136.5 g, 0.58 mol) in Et$_2$O (350 ml) was then added dropwise over 15 min, holding the temperature below −60° C. and the mixture was stirred for 2 h, allowing the temperature to rise to −40° C. The reaction was quenched by addition of saturated aqueous NH$_4$Cl solution (250 ml), warmed to ambient temperature and separated. The aqueous phase was extracted with Et$_2$O (2×250 ml) and the combined organics washed with further saturated aq. NH$_4$Cl (250 ml), dried over anhydrous MgSO$_4$ and concentrated in vacuo. The residue was diluted with isohexane (150 ml) and washed with 2 N hydrochloric acid (3×100 ml), followed by 37% hydrochloric acid (3×50 ml). The acid washings were then extracted with isohexane (3×100 ml), basified to pH 14 by careful addition of 4 N aqueous NaOH solution (500 ml) and re-extracted with CH$_2$Cl$_2$ (3×150 ml). The organic fractions were dried over anhydrous MgSO$_4$ and concentrated in vacuo. The residue was purified by distillation (bp 74-82° C., 1 atm) to afford 2-chloro-3-fluoropyridine as a straw-coloured oil (42.6 g, 63%): δ$_H$ (400 MHz, CDCl$_3$) 7.25-7.30 (1H, m), 7.47-7.51 (1H, m), 8.24 (1H, dd, J 0.8 and 4.7); m/z (ES$^+$) 132 (100%, [MH]$^+$).

A mixture of 2-chloro-3-fluoropyridine (21.0 g, 0.16 mol), benzophenone imine (32.3 g, 0.18 mol), Cs$_2$CO$_3$ (73.0 g, 0.23 mol), BINAP (5.96 g, 9.6 mmol), palladium(II) acetate (1.45 g, 6.4 mmol) and toluene (370 ml) were heated to 95° C. for 42 h, then cooled, filtered and the residue extracted with further toluene (2×210 ml). The filtrate was washed with 0.5 N hydrochloric acid (200 ml) and saturated aqueous NaHCO$_3$ (200 ml), dried over anhydrous MgSO$_4$ and concentrated in vacuo, affording crude benzhydrylidene(3-fluoropyridin-2-yl)amine as a brown oil (49.4 g) which was used directly without further purification: m/z (ES$^+$) 277 (100%, [MH]$^+$)

A mixture of crude benzhydrylidene(3-fluoropyridin-2-yl)amine (49.4 g), 2-bromoacetaldehyde diethyl acetal (56 ml, 0.37 mol), 48% hydrobromic acid (20 ml) and water (20 ml) were heated to 90° C. for 20 min. On cooling, the mixture was diluted with isopropanol (450 ml), NaHCO$_8$ (68 g) was added cautiously, and the mixture filtered. The residue was washed with further isopropanol (450 ml) and the combined organics were stirred and heated to 50° C. for 18 h. On cooling, the solution was concentrated in vacuo and azeotroped with EtOAc (2×440 ml). The remaining mixture was suspended in EtOAc (400 ml), filtered and the residue washed with further EtOAc until the filtrate ran clear (1 l). The solid orange-coloured residue was then suspended between water (100 ml) and EtOAc (220 ml) and the aqueous phase pH adjusted to 8-9 by addition of saturated aqueous NaHCO$_3$ solution (450 ml). The phases were separated and the aqueous extracted with further EtOAc (2×220 ml). The combined organic extracts were dried over anhydrous MgSO$_4$ and concentrated in vacuo affording crude 8-fluoroimidazo[1,2-α]pyridine. Purification was achieved by dissolving the crude material in EtOAc (1 l) and extracting with 2 N hydrochloric acid (5×50 ml). The acid washings were back-extracted with EtOAc (3×100 ml), adjusted to pH 11-12 using 4 N aqueous sodium hydroxide solution and re-extracted with EtOAc (5×100 ml). The combined organic fractions were washed with brine, dried over anhydrous MgSO$_4$ and concentrated in vacuo to afford 8-fluoroimidazo[1,2-α]pyridine (11.4 g, 76% from 2-chloro-3-fluoropyridine): δ$_H$ (400 MHz, CDCl$_3$) 6.69-6.74 (1H, m), 6.84-6.87 (1H, m), 7.65-7.66 (2H, m), 7.97 (1H, dd, J 1.0 and 6.8); m/z (ES$^+$) 137 (100%, [MH]$^+$).

8-Fluoroimidazo[1,2-α]pyridine (68 mg, 0.50 mmol), 2-chloro-6-trifluoromethylpyridine (182 mg, 1.0 mmol), Cs$_2$CO$_3$ (326 mg, 1.0 mmol), tetrakis(triphenylphosphine)palladium(0) (57 mg, 0.05 mmol) and 1,4-dioxane (3 ml) were heated to 150° C. for 800 s in a Smith Personal Synthesiser™ using microwave irradiation. On cooling, the mixture was partitioned between CH$_2$Cl$_2$ (2 ml) and water (2 ml), and the phases separated using a Whatman™ 5 μm teflon filter tube. The organics were concentrated in vacuo and purified by column chromatography (silica; 90% EtOAc/isohexane), yielding the title imidazopyridine as a white amorphous solid (85 mg, 60%): δ$_H$ (400 MHz; DMSO) 7.19-7.24 (1H, m), 7.38-7.43 (1H, m), 7.83 (1H, d, J 7.4), 8.20 (1H, t, J 8.2), 8.38 (1H, s), 8.64 (1H, s), 9.64 (1H, dd, J 1.2 and 7.0); m/z (ES$^+$) 282 (100%, [MH]$^+$).

EXAMPLE 2

8-Fluoro-3-(2-trifluoromethylpyrimidin-4-yl)imidazo[1,2-α]pyridine

8-Fluoroimidazo[1,2-α]pyridine (68 mg, 0.50 mmol) was coupled with 4-chloro-2-trifluoromethylpyrimidine (183 mg, 1.0 mmol) as described in Example 1, yielding semi-pure product. Further purification was achieved by washing the solid with a 1:1 mixture of Et$_2$O and isohexane, affording the title imidazopyridine as a white amorphous solid (15 mg, 11%): δ$_H$ (400 MHz; DMSO) 7.31-7.36 (1H, m), 7.51-7.56 (1H, m), 8.40 (1H, d, J 5.7), 8.90 (1H, s), 9.03 (1H, d, J 5.7), 9.65 (1H, dd, J 0.8 and 7.0); m/z (ES$^+$) 283 (100%, [MH]$^+$).

EXAMPLE 3

2-[8-Fluoro-3-(2-trifluoromethylpyrimidin-4-yl)imidazo[1,2-α]pyridin-7-yl]propan-2-ol A mixture of lithium diisopropylamide (2 M in heptane/THF/ethylbenzene, stabilised with 0.5% w/w LiBr; 1.9 ml, 3.8 mmol) and THF (3 ml) was cooled to −78° C. and a solution of 2-chloro-3-fluoropyridine (500 mg, 3.8 mmol) in THF (3 ml) was added dropwise over 1 min. After 2 h, acetone (1re-dried twice over activated 4 Å molecular sieves) was added dropwise and the mixture allowed to warm to ambient temperature, then quenched with saturated aqueous NH$_4$Cl solution (10 ml) and extracted with EtOAc (50 ml). The organic phase was dried over anhydrous MgSO$_4$ and concentrated in vacuo. The crude material was purified by column chromatography (silica; 10-20% EtOAc/isohexane) to afford 2-(2-chloro-3-fluoropyridin-4-yl)propan-2-ol (687 mg, 95%): δ$_H$ (360 MHz, CDCl$_3$) 1.66 (6H, s), 7.53 (1H, m), 8.16 (1H, m); m/z (ES$^+$) 190 (100%, [MH]$^+$).

2-(2-Chloro-3-fluoropyridin-4-yl)propan-2-ol (687 mg, 3.6 mmol) was converted to 2-(8-fluoroimidazo[1,2-α]pyridin-7-yl)propan-2-ol (240 mg, 34%) as described in Example 1: δ$_H$ (360 MHz, CDCl$_3$) 1.71 (6H, s), 7.14 (1H, t, J 6.8), 7.58-7.61 (2H, m), 7.91 (1H, d, J 7.1); m/z (ES$^+$) 195 (100%, [MH]$^+$).

2-(8-Fluoroimidazo[1,2-α]pyridin-7-yl)propan-2-ol (1.00 g, 5.2 mmol) was brominated by treatment with bromine in methanol, in the presence of potassium bromide and sodium acetate, affording 2-(3-bromo-8-fluoroimidazo[1,2-α]pyridin-7-yl)propan-2-ol (637 mg, 45%): δ$_H$ (360 MHz, CDCl$_3$) 1.72 (6H, s), 7.32 (1H, t, J 6.9), 7.59 (1H, s), 7.89 (1H, d, J 7.3); m/z (ES$^+$) 275 (100%, [M]$^+$), 273 (100).

Hünig's base (0.44 ml, 3.8 mmol) and triethylsilyl trifluoromethane-sulfonate (0.57 ml, 2.6 mmol) were added sequentially to a cold (−78° C.), stirred solution of 2-(3-bromo-8-fluoroimidazo[1,2-α]pyridin-7-yl)propan-2-ol (637 mg, 2.3 mmol) in CH$_2$Cl$_2$ (13 ml) and the solution warmed to ambient temperature. The mixture was partitioned between CH$_2$Cl$_2$ (50 ml) and water (50 ml) and the organic phase dried over anhydrous MgSO$_4$, filtered through a short plug of silica (eluent CH$_2$Cl$_2$) and concentrated to afford 3-bromo-8-fluoro-7-[2-(triethylsilyloxy)prop-2-yl]imidazo[1,2-α]pyridine (906 mg, quant.): δ$_H$ (360 MHz, CDCl$_3$) 0.70 (6H, q, J 7.8), 0.99 (9H, t, J 7.8), 1.71 (6H, s), 7.32 (1H, t, J 6.9), 7.59 (1H, s), 7.88 (1H, d, J 7.3).

Isopropylmagnesium chloride (2.0 M in THF; 0.53 ml, 1.1 mmol) was added dropwise to a stirred, cold (−78° C.) solution of 3-bromo-8-fluoro-7-[2-(triethylsilyloxy)prop-2-yl]imidazo[1,2-α]pyridine (4.0 g, 10.3 mmol) in THF. After 30 min, tri-n-butyltin chloride (0.30 ml, 1.1 mmol) was added in a single portion and the mixture was stirred for 1 h, then warmed to ambient temperature. The resulting solution of 8-fluoro-3-(tri-n-butylstannyl)-7-[2-(triethylsilyloxy)prop-2-yl]imidazo[1,2-α]pyridine in THF (circa 0.2 M) was used directly without isolation.

2-Trifluoromethyl-4-chloropyrimidine (100 mg, 0.55 mmol) and tetrakis(triphenylphosphine)palladium(0) (25 mg, 0.022 mmol) were combined with a THF solution of 8-fluoro-3-(tri-n-butylstannyl)-7-[2-(triethylsilyloxy)prop-2-yl]imidazo[1,2-α]pyridine (circa 0.2 M; 3 ml, circa 0.6 mmol) and heated to reflux, with stirring, for 3 h. After cooling, the solution was concentrated onto silica and purified by column chromatography (silica; 50% EtOAc/isohexane), then the silyl protection removed by treatment with an ethanolic solution of 37% hydrochloric acid (5 drops in 2 ml of ethanol), affording the title compound as a white amorphous solid: δ$_H$ (360 MHz, CDCl$_3$) 1.77 (6H, s), 7.48 (1H, m), 7.78 (1H, d, J 5.6), 8.42 (1H, s), 9.42 (1H, m), 9.71 (1H, d, J 7.6); m/z (ES$^+$) 341 (100%, [MH]$^+$).

EXAMPLE 4

4-Fluoro-2-{6-[8-fluoro-7-(1-hydroxy-1-methylethyl)imidazo[1,2-α]pyridin-3-yl]pyridin-2-yl]benzonitrile A mixture of 4-fluoro-2-bromobenzonitrile (10.0 g, 50.0 mmol), potassium acetate (9.82 g, 100 mmol), bis(pinacolato)diboron (14.0 g, 55.0 mmol) and dichloro[1,1'-bis(diphenylphosphino)ferrocene]palladium(II) dichloromethane adduct (0.82 g, 1.0 mmol) in 1,4-dioxane (150 ml containing 3 ml dimethylsulfoxide) was degassed with nitrogen for 1 h then heated at 85° C. for 20 h. The reaction was cooled to ambient temperature and then concentrated in vacuo. The residue was stirred with 2N sodium hydroxide (250 ml) for 10 min then filtered. The filtrate was extracted with diethyl ether (300 ml) and the organics discarded. The aqueous component was cooled to 0° C. then treated with 5N hydrochloric acid added dropwise over 15 min until pH 8. The aqueous phase was extracted with ethyl acetate (2×200 ml), the combined organics were dried over anhydrous sodium sulfate, filtered and evaporated to afford 4-fluoro- 2-(4,4,5,5-tetramethyl-[1,3,2]dioxaborolan-2-yl)benzonitrile (10.9 g, 88%) as a pale brown solid: $\delta_H$ (360 MHz, CDCl$_3$) 1.38 (12H, s), 7.15-7.25 (1H, m), 7.53-7.60 (1H, m), 7.67-7.75 (1H, m).

2,6-Dibromopyridine (0.94 g, 4.0 mmol), 4-fluoro-2-(4,4,5,5-tetramethyl-[1,3,2]dioxaborolan-2-yl)benzonitrile (1.48 g, 6.0 mmol) and potassium phosphate (1.70 g, 8.0 mmol) were dissolved in N,N-dimethylformamide (12 ml) and degassed with nitrogen for 15 min. Tetrakis(triphenylphosphine)palladium(0) (230 mg, 0.2 mmol) was added then the mixture heated at 80° C. for 16 h. The mixture was allowed to cool to ambient temperature, diluted with water (150 ml) and extracted into ethyl acetate (2×150 ml). The combined organics were washed with brine (100 ml), dried over anhydrous sodium sulfate and evaporated to give a yellow oil. Purification by flash column chromatography on silica eluting with isohexane on a gradient of ethyl acetate (10-15%) gave 4-fluoro-2-(6-bromopyridin-2-yl)benzonitrile (0.42 g, 38%) as a waxy solid: $\delta_H$ (360 MHz, CDCl$_3$) 7.21-7.25 (1H, m), 7.59 (1H, d, J 8), 7.67 (1H, dd, J 9.3, 2.6), 7.72 (1H, t, J 7.7), 7.78-7.87 (2H, m).

A mixture of 2-(8-fluoroimidazo[1,2-α]pyridin-7-yl)propan-2-ol (97 mg, 0.5 mmol), 4-fluoro-2-(6-bromopyridin-2-yl)benzonitrile (166 mg, 0.6 mmol) and Cs$_2$CO$_3$ (538 mg, 1.65 mmol) in 1,4-dioxane (4 ml) was degassed with nitrogen for 30 min. Tetrakis(triphenylphosphine)-palladium(0) (29 mg, 0.03 mmol) was added and the mixture heated under reflux for 56 h. On cooling, the mixture was partitioned between ethyl acetate (100 ml) and water (100 ml). The organics were washed with water (100 ml) and brine (50 ml), dried over anhydrous sodium sulfate, filtered and concentrated in vacuo to give an orange oil. The oil was purified by flash column chromatography on silica, eluting with dichloromethane (+1% 0.880 ammonia solution) on a gradient of methanol (2-3%). Collecting appropriate fractions followed by trituration with diethyl ether (5 ml) gave the title imidazopyridine as a white amorphous solid (131 mg, 67%): $\delta_H$ (400 MHz, CDCl$_3$) 1.74 (6H, d, J 1.2), 2.07 (1H, s), 7.26-7.30 (2H, m), 7.56-7.63 (2H, m), 7.85-7.94 (3H, m), 8.22 (1H, s), 9.74 (1H, d, J 7.4); m/z (ES$^+$) 391 (100%, [MH]$^+$).

EXAMPLE 5

5-Fluoro-2-[6-[8-fluoro-7-(1-hydroxy-1-methylethyl)imidazo[1,2-α]pyridin-3-yl]pyridin-2-yl]benzonitrile 5-Fluoro-2-(6-bromopyridin-2-yl)benzonitrile was synthesised following the procedure in Example 4.

2-(8-Fluoroimidazo[1,2-α]pyridin-7-yl)propan-2-ol (97 mg, 0.5 mmol) was coupled with 5-fluoro-2-(6-bromopyridin-2-yl)benzonitrile (166 mg, 0.6 mmol), as described in Example 4, affording the title imidazopyridine as a white amorphous solid (127 mg, 65%): $\delta_H$ (400 MHz, CDCl$_3$) 1.74 (6H, d, J 1.2), 2.08 (1H, d, J 1.2), 7.26 (1H, t, J 7.2), 7.44-7.48 (1H, m), 7.56-7.59 (2H, m), 7.82-7.84 (2H, m), 7.91 (1H, t, J 8.0), 8.21 (1H, s), 9.74 (1H, d, J 7.0); m/z (ES$^+$) 391 (100%, [MH]$^+$).

EXAMPLE 6

3-Fluoro-2-{6-[8-fluoro-7-(1-hydroxy-1-methylethyl)imidazo[1,2-α]pyridin-3-yl]pyridin-2-yl}benzonitrile 2-(8-Fluoroimidazo[1,2-α]pyridin-7-yl)propan-2-ol (194 mg, 1.0 mmol) was coupled with 2,6-dibromopyridine (403 mg, 1.7 mmol) using Cs$_2$CO$_3$ (652 mg, 2.0 mmol), as described in Example 4, affording 2-[3-(6-bromopyridin-2-yl)-8-fluoroimidazo[1,2-α]pyridin-7-yl]propan-2-ol as a white amorphous solid (210 mg, 60%): m/z (ES$^+$) 350, 352 (100%, [MH]$^+$).

2-[3-(6-Bromopyridin-2-yl)-8-fluoroimidazo[1,2-α]pyridin-7-yl]propan-2-ol (50 mg, 0.143 mmol), 3-fluoro-2-(4,4,5,5-tetramethyl-[1,3,2]dioxaborolan-2-yl)benzonitrile (53 mg, 0.214 mmol) and tetrakis(triphenylphosphine)palladium(0) (8.3 mg, 0.0714 mmol) were suspended in 1,2-dimethoxyethane (3 ml) and 2N sodium carbonate solution (0.5 ml) and heated to 150° C. for 900 s in a Smith Personal Synthesiser™ using microwave irradiation. The mixture was allowed to cool to ambient temperature, diluted with water (75 ml) and extracted into ethyl acetate (2×75 ml). The combined organic phase was washed with water (50 ml) and brine (50 ml), dried over anhydrous sodium sulfate, filtered and evaporated to give an orange oil. The oil was purified by preparative-plate chromatography on silica eluting with dichloromethane:methanol:0.880 ammonia (97:3:0.3). Collecting the appropriate fraction followed by trituration with diethyl ether (5 ml) and recrystallisation from ethyl acetate-isohexane gave the title imidazopyridine as a white amorphous solid (20 mg, 36%): $\delta_H$ (360 MHz, CDCl$_3$) 1.73 (6H, s), 2.07 (1H, d, J 1.1), 7.25 (1H, t, J 7.0), 7.46-7.59 (3H, m), 7.69 (1H, s), 7.84-7.94 (2H, m), 8.20 (1H, s), 9.72 (1H, d, J 7.4); m/z (ES$^+$) 391 (100%, [MH]$^+$).

EXAMPLE 7

2-{3-[2-(3,4-Difluorophenyl)pyrimidin-4-yl]-8-fluoroimidazo[1,2-α]pyridin-7-yl}propan-2-ol Isopropylmagnesium chloride (2.0M in THF; 5.7 ml, 11.4 mmol) was added dropwise to a stirred, cold (−78° C.) solution of 3-bromo-8-fluoro-7-[2-(triethylsilyloxy)prop-2-yl]imidazo[1,2-α]pyridine (4.0 g, 10.3 mmol) in THF (80 ml). After 10 min, tri-n-butyltin chloride (3.22 ml, 11.9 mmol) was added in a single portion and the mixture was stirred for 30 min, then warmed to ambient temperature. 2,4-Dichloropyrimidine (2.31 g, 15.5 mmol) was added and the mixture degassed by bubbling through N$_2$. Tetrakis (triphenylphosphine)palladium(0) (1.19 g, 1.03 mmol) and copper(I) iodide (19.7 mg, 0.1 mmol) were then added in single portions and the reaction was heated to reflux for 18 h. On cooling, water (80 ml) was added and the phases separated. The aqueous was extracted with EtOAc (40 ml) and the combined organics washed with brine (40 ml), dried over MgSO$_4$, filtered and concentrated in vacuo. Purified by column chromatography (silica, 0 to 5% MeOH in CH$_2$Cl$_2$) and the semi-pure product washed with 1:2 Et$_2$O/isohexane to afford 3-(2-chloropyrimidin-4-yl)-8-fluoro-7-[2-(triethylsilyloxy)prop-2-yl]imidazo[1,2-α]pyridine as a white amorphous solid (3.4 g): m/z (ES$^+$) 421 (100%, [MH]$^+$) and 423 (30).

3,4-Difluorophenylboronic acid (90 mg, 0.57 mmol), 3-(2-chloropyrimidin-4-yl)-8-fluoro-7-[2-(triethylsilyloxy)prop-2-yl]imidazo[1,2-α]pyridine (120 mg, 0.29 mmol), tetrakis(triphenylphosphine)palladium(0) (16 mg, 0.015 mmol), THF (1.4 ml) and aqueous Na$_2$CO$_3$ solution (2M; 0.44 ml) were combined and heated to reflux for 18 h. On cooling, the mixture was partitioned between 2M NaOH solution (2 ml) and CH$_2$Cl$_2$ (3 ml) and the phases separated using a phase-separation cartridge. The organic fraction was purified by column chromatography (silica, 90% EtOAc/isohexane), then the silyl protection removed by treatment with an ethanolic solution of 37% hydrochloric acid (5 drops in 2 ml of ethanol). After 48 h, the solution was concentrated in vacuo and the residue partitioned between EtOAc and saturated aqueous NaHCO$_3$. The organic phase was dried over MgSO$_4$, filtered, concentrated and the residue purified by column chromatography (silica, EtOAc) affording the title compound as a white amorphous solid (158 mg): $\delta_H$ (360 MHz, CDCl$_3$) 1.76 (6H, s), 7.00-7.20 (2H, m), 7.40-7.70 (2H, m), 8.20-8.40 (1H, m), 8.36 (1H, s), 8.80 (1H, m), 9.90-9.92 (1H, m); m/z (ES$^+$) 385 (100%, [MH]$^+$).

EXAMPLES 8 TO 22

The following compounds were prepared by analogous methods:

EXAMPLE 8

2-{3-[2-(2,3-Difluorophenyl)pyrimidin-4-yl]-8-fluoroimidazo[1,2-α]pyridin-7-yl}propan-2-ol m/z (ES$^+$) 385 (100%, [MH]$^+$)

EXAMPLE 9

2-{3-[2-(2,4-Difluorophenyl)pyrimidin-4-yl]-8-fluoroimidazo[1,2-α]pyridin-7-yl}propan-2-ol m/z (ES$^+$) 385 (100%, [MH]$^+$)

EXAMPLE 10

2-{8-Fluoro-3-[2-(3-fluorophenyl)pyrimidin-4-yl]imidazo[1,2-α]pyridin-7-yl}propan-2-ol m/z (ES$^+$) 367 (100%, [MH]$^+$)

EXAMPLE 11

2-{3-[2-(4-Chloro-3-fluorophenyl)pyrimidin-4-yl]-8-fluoroimidazo[1,2-α]pyridin-7-yl}propan-2-ol m/z (ES$^+$) 401 (100%, [MH]$^+$)

EXAMPLE 12

2-{3-[2-(3-Chloro-6-fluorophenyl)pyrimidin-4-yl]-8-fluoroimidazo[1,2-α]pyridin-7-yl}propan-2-ol m/z (ES$^+$) 401 (100%, [MH]$^+$)

EXAMPLE 13

2-{3-[2-(3-Chloro-2-fluorophenyl)pyrimidin-4-yl]-8-fluoroimidazo[1,2-α]pyridin-7-yl}propan-2-ol m/z (ES$^+$) 401 (100%, [MH]$^+$)

EXAMPLE 14

2-{3-[2-(3-Chloro-4-fluorophenyl)pyrimidin-4-yl]-8-fluoroimidazo[1,2-α]pyridin-7-yl}propan-2-ol m/z (ES$^+$) 401 (100%, [MH]$^+$)

EXAMPLE 15

2-{3-[2-(4-Chlorophenyl)pyrimidin-4-yl]-8-fluoroimidazo[1,2-α]pyridin-7-yl}propan-2-ol m/z (ES$^+$) 383 (100%, [MH]$^+$)

EXAMPLE 16

2-{3-[2-(2,4-Dichlorophenyl)pyrimidin-4-yl]-8-fluoroimidazo[1,2-α]pyridin-7-yl}propan-2-ol m/z (ES$^+$) 417 (100%, [MH]$^+$)

EXAMPLE 17

4-{4-[8-Fluoro-7-(2-hydroxyprop-2-yl)imidazo[1,2-α]pyridin-3-yl]pyrimidin-2-yl}benzonitrile m/z (ES$^+$) 374 (100%, [MH]$^+$)

EXAMPLE 18

3-{4-[8-Fluoro-7-(2-hydroxyprop-2-yl)imidazo[1,2-α]pyridin-3-yl]pyrimidin-2-yl}benzonitrile m/z (ES$^+$) 374 (100%, [MH]$^+$)

EXAMPLE 19

6-Fluoro-3-{4-[8-fluoro-7-(2-hydroxyprop-2-yl)imidazo[1,2-α]pyridin-3-yl]pyrimidin-2-yl}benzonitrile m/z (ES$^+$) 392 (100%, [MH]$^+$)

EXAMPLE 20

2-Fluoro-4-{4-[8-fluoro-7-(2-hydroxyprop-2-yl)imidazo[1,2-α]pyridin-3-yl]pyrimidin-2-yl}benzonitrile m/z (ES$^+$) 392 (100%, [MH]$^+$)

EXAMPLE 21

5-Fluoro-2-{4-[8-fluoro-7-(2-hydroxyprop-2-yl)imidazo[1,2-α]pyridin-3-yl]pyrimidin-2-yl}benzonitrile m/z (ES$^+$) 392 (100%, [MH]$^+$)

EXAMPLE 22

5-Fluoro-2-{4-[8-fluoro-7-(2-hydroxyprop-2-yl)imidazo[1,2-α]pyridin-3-yl]pyrimidin-2-yl}benzamide m/z (ES$^+$) 410 (100%, [MH]$^+$)

EXAMPLE 23

5-Fluoro-2-{3-fluoro-6-[8-fluoro-7-(2-hydroxyprop-2-yl)imidazo[1,2-α]pyridin-3-yl]pyridin-2-yl}benzonitrile To a degassed solution of 5-fluoro-2-(4,4,5,5-tetramethyl-[1,3,2]dioxaborolan-2-yl)benzonitrile (5.55 g, 22.46 mmol), 2-chloro-3-fluoropyridine (2.95 g, 22.46 mmol), potassium fluoride (4.3 g, 74.14 mmol) and tris(dibenzylideneacetone)dipalladium(0) (0.824 g, 0.89 mmol) in THF (80 ml) and water (8 ml) was added tri(tert-butyl)phosphine (0.51M solution in hexane; 3.52 ml, 1.79 mmol). The reaction was heated at 70° C. for 48 h, then allowed to cool to ambient temperature. The reaction mixture was filtered through a catalyst filter, and the filtrate diluted with ethyl acetate (400 ml) and washed with water (2×100 ml). The organic phase was separated, dried (MgSO$_4$), filtered and adsorbed onto silica gel. The crude product was chromatographed on silica, eluting with 10% ethyl acetate in isohexane, to give 5-fluoro-2-(3-fluoropyridin-2-yl)benzonitrile as a white solid (3.02 g): δ$_H$ (400 MHz, CDCl$_3$) 7.40-7.45 (2H, m), 7.51-7.61 (2H, m), 7.72-7.76 (1H, m), 8.58-8.60 (1H, m); m/z (ES$^+$) 217.

To a solution of 5-fluoro-2-(3-fluoropyridin-2-yl)benzonitrile (1 g, 4.62 mmol) in dichloromethane (10 ml) at 0° C. was added urea hydrogen peroxide addition compound (0.91 g, 9.71 mmol) followed by trifluoroacetic anhydride (1.94 g, 1.30 ml, 9.25 mmol) and the mixture warmed to ambient temperature and stirred for 18 h. The reaction was quenched with Na$_2$S$_2$O$_3$ (saturated solution; 2 ml) and poured onto 0.5N HCl (20 ml). The aqueous phase was extracted with dichloromethane (2×100 ml) and the combined organics dried over MgSO$_4$, filtered and evaporated to give a red oil. The crude product was chromatographed on silica (0 to 5% methanol in dichloromethane) to give 5-fluoro-2-(3-fluoro-1-oxypyridin-2-yl)benzonitrile as an amber oil which crystallised on standing (0.687 g): δ$_H$ (400 MHz, CDCl$_3$) 7.24-7.27 (1H, m), 7.36-7.39 (1H, m), 7.45-7.49 (1H, m), 7.56 (1H, dd, J 2.7, 7.8), 7.65 (1H, dd, J 6.3, 8.7), 8.29 (1H, d, J 6.6); m/z (ES$^+$) 233.

To a solution of 5-fluoro-2-(3-fluoro-1-oxypyridin-2-yl)benzonitrile (0.67 g, 2.88 mmol) in chloroform (3 ml) was added phosphorus oxychloride (11.06 g, 72.18 mmol) and the mixture heated at reflux for 2 h. After cooling to ambient temperature, the reaction was poured onto ice (150 g) and stirred for 15 mins. Solid sodium carbonate was then added portionwise until pH=10. The mixture was then extracted with dichloromethane (2×150 ml) and the combined organics dried (MgSO$_4$), filtered and evaporated to give a cream-coloured solid. The crude product was chromatographed on silica, eluting with 50-25% isohexane in dichloromethane, to give two products. Less polar product 2-(6-chloro-3-fluoropyridin-2-yl)-5-fluorobenzonitrile (258 mg): δ$_H$ (400 MHz, CDCl$_3$) 7.41-7.45 (2H, m), 7.53 (1H, dd, J 2.6, 7.9), 7.57 (1H, t, J 8.6), 7.74 (1H, dd, J 5.4, 8.8); m/z (ES$^+$) 251. More polar product 2-(4-chloro-3-fluoropyridin-2-yl)-5-fluorobenzonitrile (115 mg): δ$_H$ (400 MHz, CDCl$_3$) 7.41-7.45 (1H, m), 7.49 (1H, t, J 5.1), 7.55 (1H, dd, J 2.6, 7.9), 7.73 (1H, dd, J 1.3, 14.1), 8.47 (1H, d, J 5.1); m/z (ES$^+$) 251.

To 2-(8-fluoroimidazo[1,2-α]pyridin-7-yl)propan-2-ol (0.21 g, 1.10 mmol), 2-(6-chloro-3-fluoropyridin-2-yl)-5-fluorobenzonitrile (0.25 g, 1.00 mmol) and palladium acetate (0.011 g, 0.05 mmol) in N,N-dimethylacetamide (2 ml) was added triphenylphosphine (0.013 g, 0.05 mmol) followed by potassium acetate (0.14 g, 1.51 mmol) and the mixture heated at 130° C. for 2 h. The reaction was cooled to ambient temperature, diluted with methanol (8 ml) and 2 drops of acetic acid were added. The mixture was poured onto a strong cation exchange cartridge and eluted with several column lengths of methanol. Several column lengths of 2N ammonia in methanol were then eluted to recover the product. The pale yellow oil was chromatographed on silica, eluting with 3% methanol in dichloromethane, to give the title material as a white powdery solid. Recrystallised from ethyl acetate/ether to afford the title compound (215 mg): δ$_H$ (400 MHz, CDCl$_3$) 1.73 (6H, s), 2.07 (1H, s), 7.26 (1H, d, J 14.4), 7.45-7.49 (1H, m), 7.61 (1H, dd, J 2.6, 7.9), 7.67 (1H, t, J 9.0), 7.77-7.80 (1H, m), 7.88 (1H, dd, J 3.3, 8.9), 8.15 (1H, s), 9.59 (1H, d, J 7.3); m/z (ES$^+$) 409.

EXAMPLES 24 TO 26

The following compounds were prepared by analogous methods:

EXAMPLE 24

4-Fluoro-2-{3-fluoro-6-[8-fluoro-7-(2-hydroxyprop-2-yl)imidazo[1,2-α]pyridin-3-yl]pyridin-2-yl}benzonitrile m/z (ES$^+$) 409.

EXAMPLE 25

4-Fluoro-2-{3-fluoro-4-[8-fluoro-7-(2-hydroxyprop-2-yl)imidazo[1,2-α]pyridin-3-yl]pyridin-2-yl}benzonitrile m/z (ES$^+$) 409.

EXAMPLE 26

5-Fluoro-2-{3-fluoro-4-[8-fluoro-7-(2-hydroxyprop-2-yl)imidazo[1,2-α]pyridin-3-yl]pyridin-2-yl}benzonitrile m/z (ES$^+$) 409.

EXAMPLE 27

5-Fluoro-2-{4-[8-fluoro-7-(2-hydroxyprop-2-yl)imidazo[1,2-α]pyridin-3-yl]pyridin-2-yl}benzonitrile 2-(8-Fluoroimidazo[1,2-α]pyridin-7-yl)propan-2-ol was coupled to 2-(4-chloropyridin-2-yl)-5-fluorobenzonitrile (prepared from 5-fluoro-2-(4,4,5,5-tetramethyl-[1,3,2]dioxaborolan-2-yl)benzonitrile and 2,4-dichloropyridine by an analogous procedure to that described in WO 02/076983), by the method of Example 23, to give 5-fluoro-2-{4-[8-fluoro-7-(2-hydroxyprop-2-yl)imidazo[1,2-α]pyridin-3-yl]pyridin-2-yl}benzonitrile: δ$_H$ (500 MHz, CDCl$_3$) 1.75 (6H, s), 2.08 (1H, s), 7.32 (1H, t, J 7.0), 7.45-7.49 (1H, m), 7.53-7.56 (2H, m), 7.92 (1H, s), 7.98 (1H, t, J 0.7), 7.99 (1H, dd, J 3.4, 5.4), 8.50 (1H, d, J 7.3), 8.87 (1H, d, J 5.1); m/z (ES$^+$) 391. Also isolated from the above reaction was 5-fluoro-2-{4-[8-fluoro-7-(2-hydroxyprop-2-yl)imidazo[1,2-α]pyridin-3-yl]pyridin-2-yl}benzamide: δ$_H$ (500 MHz, DMSO) 1.59 (6H, s), 7.35-7.44 (3H, m), 7.60 (1H, t, J 0.6), 7.66 (1H, dd, J 0.5, 0.7), 7.82-7.84 (1H, m), 7.85 (1H, s), 7.95 (1H, s), 8.05 (1H, s), 8.60 (1H, d, J 7.1), 8.73 (1H, d, J 5.4); m/z (ES$^+$) 409.

EXAMPLES 28 AND 29

The following compounds were prepared by analogous methods:

EXAMPLE 28

2-{8-Fluoro-3-[2-(3-fluorophenyl)pyridin-4-yl]imidazo[1,2-α]pyridin-7-yl}propan-2-ol m/z (ES$^+$) 366.

EXAMPLE 29

3-Fluoro-2-{4-[8-fluoro-7-(2-hydroxyprop-2-yl)
imidazo[1,2-α]pyridin-3-yl]pyridin-2-yl}benzamide m/z (ES⁺) 409.

EXAMPLE 30

5-Fluoro-2-{5-[8-fluoro-7-(2-hydroxyprop-2-yl)
imidazo[1,2-α]pyridin-3-yl]pyridin-3-
yl}benzonitrile A solution of 3,5-dibromopyridine (1.0 g, 4.2 mmol) and 5-fluoro-2-(4,4,5,5-tetramethyl-[1,3,2]dioxaborolan-2-yl)benzonitrile (0.95 g, 3.8 mmol) in 1,2-dimethoxyethane (20 ml) and 2N sodium carbonate solution (10 ml) was degassed with nitrogen for 30 min. Tetrakis-(triphenylphosphine)palladium(0) (89 mg, 0.08 mmol) was added and the mixture heated under reflux for 18 h. The mixture was allowed to cool to ambient temperature, diluted with water (10 ml) then extracted with ethyl acetate (2×100 ml). The organics were combined, dissolved in phophorus oxychloride (50 ml) and heated at 100° C. for 2 h. The reaction mixture was allowed to cool to ambient temperature and concentrated. The residue was treated with ice, and the resulting solution was layered with ethyl acetate (30 ml) and made basic by the addition of solid sodium hydrogencarbonate. The layers were separated, and the aqueous extracted further with ethyl acetate (75 ml). The organics were combined, washed with brine (20 ml), dried over anhydrous magnesium sulfate, filtered and evaporated to give a colourless oil. The oil was purified by flash column chromatography on silica, eluting with isohexane on a gradient of ethyl acetate (20-50%), to give 2-(5-bromopyridin-3-yl)-5-fluorobenzonitrile (0.95 g, 81%) as a white solid: δ$_H$ (360 MHz, CDCl₃) 7.44-7.46 (1H, m), 7.49-7.54 (2H, m), 8.02 (1H, s), 8.67 (1H, d, J 1.8), 8.78 (1H, d, J 1.8).

2-(8-Fluoroimidazo[1,2-α]pyridin-7-yl)propan-2-ol (145 mg, 0.75 mmol) and 2-(5-bromopyridin-3-yl)-5-fluorobenzonitrile (208 mg, 0.75 mmol) were coupled following the procedure in Example 23 to afford 5-fluoro-2-{5-[8-fluoro-7-(2-hydroxyprop-2-yl)imidazo[1,2-α]pyridin-3-yl]pyridin-3-yl}benzonitrile (152 mg, 52%) as a white solid: δ$_H$ (500 MHz, DMSO) 1.59 (6H, s), 5.57 (1H, s), 7.23 (1H, dd, J 7 and 7), 7.80 (1H, ddd, J 9, 9 and 3), 7.91-7.94 (1H, m), 7.99 (1H, s), 8.08 (1H, dd, J 9 and 3), 8.41 (1H, dd, J 2 and 2), 8.58 (1H, d, J 7), 8.82 (1H, s), 9.01 (1H, s); m/z (ES⁺) 391 (100%, [MH]⁺).

EXAMPLE 31

5-Fluoro-2-[3-fluoro-6-(8-fluoro-7-trifluoromethylimidazo[1,2-α]pyridin-3-yl)pyridin-2-yl]benzonitrile 3-Bromo-8-fluoro-7-trifluoromethylimidazo[1,2-α]pyridine was prepared and coupled with 2-(6-chloro-3-fluoropyridin-2-yl)-5-fluorobenzonitrile as described in Example 3 to give 5-fluoro-2-[3-fluoro-6-(8-fluoro-7-trifluoromethylimidazo[1,2-α]pyridin-3-yl)pyridin-2-yl]benzonitrile as an off-white solid: δ$_H$ (400 MHz, d₆-DMSO) 7.34 (1H, t, J 7), 7.72-7.85 (1H, m), 8.02 (1H, dd, J 13 and 1), 8.13-8.23 (2H, m), 8.41 (1H, dd, J 9 and 4), 8.75 (1H, s), 9.71 (1H, d, J 7).

EXAMPLE 32

5-Fluoro-2-[3-fluoro-4-(8-fluoro-7-trifluoromethylimidazo[1,2-α]pyridin-3-yl)pyridin-2-yl]benzonitrile The title compound was prepared by analogous procedures.

m/z (ES⁺) 419 [100%, MH]⁺.

The invention claimed is:

1. A compound of formula I, or a pharmaceutically acceptable salt thereof:

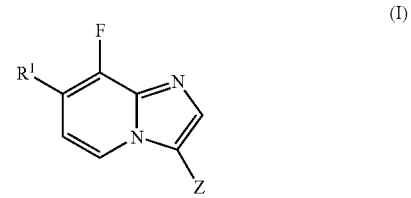

(I)

wherein:

Z represents a heteroaromatic ring which is selected from: furan, thiophene, pyrrole, oxazole, thiazole, isoxazole, isothiazole, imidazole, pyrazole, oxadiazole, thiadiazole, triazole, tetrazole, pyridine, pyrazine, pyrimidine and pyridazine, which is unsubstituted or substituted with R⁶;

R¹ is selected from the group consisting of: hydrogen, halogen, cyano, trifluoromethyl, nitro, —OR$^a$, —SR$^a$, —SOR$^a$, —SO₂R$^a$, —SO₂NR$^a$R$^b$, —NR$^a$R$^b$, —NR$^a$COR$^b$, —NR$^a$CO₂R$^b$, —COR$^a$, —CO₂R$^a$, —CONR$^a$R$^b$, —CR$^a$=NOR$^b$ (wherein R$^a$ is hydrogen or C$_{1-6}$ alkyl and R$^b$ is hydrogen, C$_{1-6}$ alkyl, hydroxy (C$_{1-6}$)alkyl or di(C$_{1-6}$) alkylamino(C$_{1-6}$)alkyl), C$_{1-6}$ alkyl, halo(C$_{1-6}$)alkyl, dihalo(C$_{1-6}$)alkyl, hydroxy (C$_{1-6}$)alkyl, C$_{1-6}$ alkoxy(C$_{1-6}$)alkyl, di(C$_{1-6}$)alkoxy (C$_{1-6}$)alkyl, cyano(C$_{1-6}$)alkyl, C$_{3-7}$ cycloalkyl, pyridinyl, quinolinyl, isoquinolinyl, pyridazinyl, pyrimidinyl, pyrazinyl, furyl, benzofuryl, dibeuzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl, isoquinolinylmethyl, halogen, cyano, trifluoromethyl, C$_{1-6}$ alkoxy, formyl, C$_{2-6}$ alkylcarbonyl, C$_{2-6}$ alkoxycarbonyl and —CR⁴=NOR⁵, wherein an alkyl or heteroaryl group in R¹ is unsubstituted or substituted with a group selected from: C$_{1-6}$ alkyl, adamantyl, phenyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, aminocarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR'R$^w$, —NR$^v$-COR$^w$, —NR$^v$CO₂R$^w$, —NR'SO₂R$^w$, —CH₂NR'SO₂R$^w$, —NHCONR'R$^w$, —CONR'R$^w$, —SO₂NR'R" and —CH₂SO₂NR'R", wherein R' and R" are independently selected from hydrogen, C$_{1-6}$ alkyl, phenyl and phenyl(C$_{1-6}$)alkyl;

R⁶ is selected from the group consisting of: halogen, cyano, trifluoromethyl, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy (C$_{1-6}$)alkyl, C$_{3-7}$ cycloalkyl, azetidinyl, pyrrolidinyl, piperidinyl, piperazinyl, morpholinyl, thiomorpholinyl, benzyl-tetrahydropyridinyl, C$_{1-6}$ alkoxy, methyltriazolyl(C$_{1-6}$)alkoxy, C$_{1-6}$ alkylthio, C$_{1-6}$ alkylsulphonyl, C$_{2-6}$ alkylcarbonyl, amino, C$_{1-6}$ alkylamino, di(C$_{1-6}$)alkylamino, C$_{2-6}$ alkylcarbonylamino, phenyl, (C$_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$)alkylcarbonyl-phenyl, trifluorothio-phenyl, (C$_{1-6}$)alkylsulphonyl-phenyl, di(C$_{1-4}$)alkylaminocarbonyl-phenyl, di(C$_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl and an unsubstituted or substituted heteroaryl group, wherein the heteroaryl group is selected from: pyridinyl, quinolinyl, isoquinolinyl, pyridazinyl, pyrimidinyl, pyrazinyl, furyl, benzofrryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl, and when the heteroaryl group is substituted, the substituents on the heteroaryl group are selected from oxy, halogen, cyano and C$_{1-6}$ alkyl.

2. The compound of claim 1 wherein Z is selected from the group consisting of: thiophene, thiazole, thiadiazole, pyridinyl and pyrimidinyl, which is unsubstituted or substituted with R⁶.

3. The compound of claim 1 wherein R⁶ is selected from the group consisting of: fluoro, chloro, bromo, iodo, cyano, trifluoromethyl, methyl, isopropyl, tert-butyl, chloromethyl, fluoropropyl, difluoroethyl, hydroxypropyl, methoxymethyl, cyclopentyl, pyrrolidinyl, morpholinyl, benzyl-tetrahydropyridinyl, oxy, hydroxy, methoxy, ethoxy, isopropoxy, tert-butoxy, methyltriazolyl-methoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolylphenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

4. The compound of claim 1 wherein R⁶ is selected from the group consisting of: fluoro, trifluoromethyl, fluorophenyl, chlorophenyl, difluorophenyl, dichlorophenyl, (chloro)(fluoro)phenyl, cyanophenyl, (cyano)(fluoro)phenyl and (aminocarbonyl)(fluoro)phenyl.

5. The compound of claim 1 of the formula IA, or a pharmaceutically acceptable salt thereof:

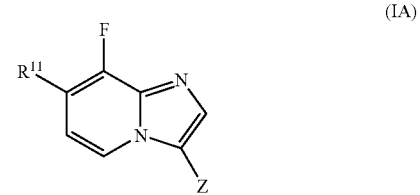

(IA)

wherein:

R¹¹ is selected from the definitions of R¹ and is a substituent selected from the group consisting of: hydrogen, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, di(C$_{1-6}$)alkoxy(C$_{1-6}$)alkyl, cyano(C$_{1-6}$)alkyl, C$_{3-7}$ cycloalkyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, flirylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl, isoquinolinylmethyl, halogen, cyano, trifluoromethyl, C$_{1-6}$ alkoxy, formyl, C$_{2-6}$ alkylcarbonyl, C$_{2-6}$ alkoxycarbonyl and —CR⁴=NOR⁵, wherein the alkyl or heteroaryl group in R¹¹ is unsubstituted or substituted with a group selected from: C$_{1-6}$ alkyl, adamantyl, phenyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, aminocarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR'R", —NR'COR", —NR'CO₂R", —NR'SO₂R", —CH₂NR'SO₂R", —NHCONR'R", —CONR'R", —SO₂NR'R" and —CH₂SO₂NR'R", wherein R' and R" are independently selected from hydrogen, C$_{1-6}$ alkyl, phenyl and phenyl(C$_{1-6}$)alkyl;

R⁴ represents hydrogen or C$_{1-6}$ alkyl; and

R⁵ represents hydrogen, C$_{1-6}$ alkyl, hydroxy(C$_{1-6}$)alkyl or di(C$_{1-6}$)alkylamino(C$_{1-6}$)alkyl.

6. The compound of claim 5 wherein R¹¹ is selected from the group consisting of: hydrogen, methyl, fluoromethyl, difluoromethyl, hydroxymethyl, methoxymethyl, dimethoxymethyl, hydroxyethyl, fluoroethyl, difluoroethyl, dimethoxyethyl, isopropyl, hydroxypropyl, fluoropropyl, cyanopropyl, tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and -CR$^2$=NOR$^3$, wherein R$^2$ represents hydrogen or methyl, and R$^3$ represents hydrogen, hydroxyethyl or dimethylaminoethyl.

7. The compound of claim 6 wherein R$^{11}$ is selected from the group consisting of: 1-hydroxyethyl, 1-fluoroethyl, 1,1-difluoroethyl, 1,1-dimethoxyethyl, 2-hydroxyprop-2-yl, 2-fluoroprop-2-yl and 2-cyanoprop-2-yl.

8. The compound of claim 5 of the formula IIA, or a pharmaceutically acceptable salt thereof:

(IIA)

wherein:

X represents CH or CF and Y represents N; or

X represents N and Y represents CH, CF or N;

R$^6$ represents a substituent selected from the group consisting of: hydrogen, halogen, cyano, trifluoromethyl, C$_{1-6}$ alkyl, halo(C$_{1-6}$)alkyl, dihalo(C$_{1-6}$)alkyl, hydroxy (C$_{1-6}$)alkyl, C$_{1-6}$ alkoxy(C$_{1-6}$)alkyl, C$_{3-7}$ cycloalkyl, azetidinyl, pyrrolidinyl, piperidinyl, piperazinyl, morpholinyl, thiomorpholinyl, benzyl-tetrahydropyridinyl, C$_{1-6}$ alkoxy, methyltriazolyl(C$_{1-6}$)alkoxy, C$_{1-6}$ alkylthio, C$_{1-6}$ alkylsulphonyl, C$_{2-6}$ alkylcarbonyl, amino, C$_{1-6}$ alkylamino, di(C$_{1-6}$)alkylamino, C$_{2-6}$ alkylcarbonylamino, phenyl, (C$_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro) phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$) alkylcarbonyl-phenyl, trifluorothio-phenyl, (C$_{1-6}$ alkylsulphonyl-phenyl, di(C$_{1-6}$)alkylaminocarbonylphenyl, di(C$_{1-6}$)alkylaminosulphonyl-phenyl, (halo) (morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolylphenyl and an unsubstituted or substituted heteroaryl group, wherein the heteroaryl group is selected from: pyridinyl, quinolinyl, isoquinolinyl, pyridazinyl, pyrimidinyl, pyrazinyl, furyl, benzofiiryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl, and when the heteroaryl group is substituted, the substituents on the heteroaryl group are selected from oxy, halogen, cyano and C$_{1-6}$ alkyl.

9. The compound of claim 8 of the formula IIB, or a pharmaceutically acceptable salt thereof:

(IIB)

wherein the phenyl ring bearing the cyano and R$^{16}$ is selected from the definitions of R$^6$ and wherein R$^{16}$ represents hydrogen or fluoro.

10. A compound which is selected from: 8-fluoro-3-(6-trifluoromethylpyridin-2-yl)imidazo[1,2-a]pyridine; 8-fluoro-3 (2-trifluoromethylpyrimidin-4-yl)imidazo[1,2-a] pyridine; 2-[8-fluoro-3-(2-trifluoromethylpyrimidin-4-yl) imidazo[1,2-a]pyridin-7-yl]propan-2-ol; 4-fluoro-2-{6-[8-fluoro-7-(1-hydroxy-1-methylethyl)imidazo[1,2-a]pyridin-3-yl]pyridin-2yl}benzonitrile; 5-fluoro-2-{6-[8-fluoro-7-(1-hydroxy-1-methylethyl)imidazo[1,2-a]pyridin-3-yl]pyridin-2-yl}benzonitrile; 3-fluoro-2-{6-[8-fluoro-7-(1-hydroxy-1-methylethyl)imidazo[1,2-a]pyridin-3yl]pyridin-2-yl}benzonitrile; or a pharmaceutically acceptable salt thereof.

11. A compound which is selected from:

2-{3-[2-(3,4-difluorophenyl)pyrimidin-4-yl]-8-fluoroimidazo[1,2-a]pyridin-7-yl }propan-2-ol;

2-{3-[2-(2,3-difluorophenyl)pyrimidin-4-yl]-8-fluoroimidazo[1,2-a]pyridin-7-yl }propan-2-ol;

2-{3-[2-(2,4-difluorophenyl)pyrimidin-4-yl]-8-fluoroimidazo[1,2-a]pyridin-7-yl }propan-2-ol;

2-{8-fluoro-3-[2-(3-fluorophenyl)pyrimidin-4-yl]imidazo[1,2-a]pyridin-7-yl}propan-2-ol;

2-{3-[2-(4-chloro-3-fluorophenyl)pyrimidin-4-yl]-8-fluoroimidazo[1,2-a]pyridin-7-yl}propan-2-ol;

2-{3-[2-(3-chloro-6-fluorophenyl)pyrimidin-4-yl]-8-fluoroimidazo[1,2-a]pyridin-7-yl}propan-2-ol;

2-{3-[2-(3-chloro-2-fluorophenyl)pynmidin-4-yl]-8-fluoroimidazo[1,2-a]pyridin-7-yl}propan-2-ol;

2-{3-[2-(3-chloro-4-fluorophenyl)pyrimidin-4-yl]-8-fluoroimidazo[1,2-a]pyridin-7-yl}propan-2-ol;

2-{3-[2-(4-cblorophenyl)pyrimidin-4-yl]-8-fluoroimidazo[1,2-a]pyridin-7-yl}propan-2-ol;

2-{3 -[2-(2,4-dichlorophenyl)pyrimidin-4-yl]-8-fluoroimidazo[1,2-a]pyridin-7-yl}propan-2-ol;

4-{4-[8-fluoro-7-(2-hydroxyprop-2-yl)imidazo[1,2-a]pyridin-3-yl]pyrimidin-2-yl}benzonitrile;

3-{4-[8-fluoro-7-(2-hydroxyprop-2-yl)imidazo[1,2-a]pyridin-3-yl]pyrimidin-2-yl}benzonitrile;

6-fluoro-3-{4-[8-fluoro-7-(2-hydroxyprop-2-yl)imidazo [1,2-a]pyridin-3-yl]pyrimidin-2-yl}benzonitrile;

2-fluoro-4-{4-[8-fluoro-7-(2-hydroxyprop-2-yl)imidazo [1,2-a]pyridin-3-yl]pyrimidin-2-yl}benzonitrile;

5-fluoro-2-{4-[8-fluoro-7-(2-hydroxyprop-2-yl)imidazo [1,2-a]pyridin-3-yl]pyrimidin-2-yl}benzonitrile;

5-fluoro-2-{4-[8-fluoro-7-(2-hydroxyprop-2-yl)imidazo [1,2-a]pyridin-3-yl]pyrimidin-2-yl}benzamide;

5-fluoro-2-{3-fluoro-6-[8-fluoro-7-(2-hydroxyprop-2-yl) imidazo]1,2-a]pyridin-3-yl]pyridin-2-yl }benzonitrile;
4-fluoro-2-{3-fluoro-6-[8-fluoro-7-(2-hydroxyprop-2-yl) imidazo[1,2-a]pyridin-3-yl]pyridin-2-yl }benzonitrile;
4-fluoro-2-{3-fluoro-4-[8-fluoro-7-(2-hydroxyprop-2-yl) imidazo[1,2-a]pyridin-3-yl]pyridin-2-yl }benzonitrile;
5-fluoro-2-{3-fluoro-4-[8-fluoro-7-(2-hydroxyprop-2-yl) imidazo[1,2-a]pyridin-3-yl]pyridin-2-yl }benzonitrile;
5-fluoro-2-{4-[8-fluoro-7-(2hydroxyprop-2-yl)imidazo [1,2-a]pyridin-3-yl]pyridin-2-yl}benzonitrile;
2-{8-fluoro-3-[2-(3-fluorophenyl)pyridin-4-yl]imidazo [1,2-a]pyridin-7-yl}propan-2-ol;
3-fluoro-2-{4-[8-fluoro-7-(2-hydroxyprop-2-yl)imidazo [1,2-a]pyridin-3-yl]pyridin-2-yl}benzamide;
5-fluoro-2-{5-[8-fluoro-7-(2-hydroxyprop-2-yl)imidazo [1,2-a]pyridin-3-yl]pyridin-3-yl}benzonitrile;
5-fluoro-2-[3-fluoro-6-(8-fluoro-7-trifluoromethylimi- dazo[1,2-a]pyridin-3-yl) pyridin-2-yl]benzonitrile;
5-fluoro-2-[3-fluoro-4-(8-fluoro-7-trifluoromethylimi- dazo[1,2-a]pyridin-3-yl) pyridin-2-yl]benzonitrile;
or a pharmaceutically acceptable salt thereof.

12. A pharmaceutical composition comprising a compound of claim 1 or a pharmaceutically acceptable salt thereof and a pharmaceutically acceptable carrier.

13. A method for the treatment of a neurological disorder which comprises administering to a patient in need of such treatment an effective amount of a compound of claim 1 or a pharmaceutically acceptable salt thereof.

14. A process for the preparation of the compound of claim 1, which comprises:

(A) reacting a compound of formula m with a compound of formula IV:

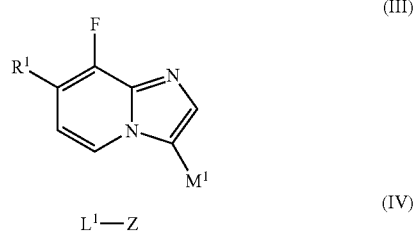

(III)

(IV)

wherein Z and $R^1$ are as defined in claim 1, $L^1$ represents a suitable leaving group, and $M^1$ represents a boronic acid moiety —$B(OH)_2$ or a cyclic ester thereof formed with an organic diol, or $M^1$ represents —Sn(Alk)$_3$ in which Alk represents $C_{1-6}$ alkyl; in the presence of a transition metal catalyst; or (B) reacting a compound of formula V with a compound of formula VI:

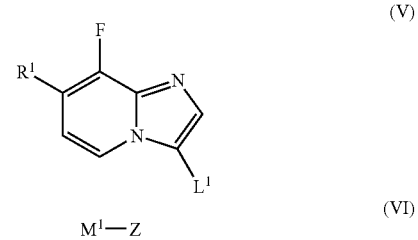

(V)

(VI)

wherein Z and $R^1$ are as defined in claim 1, and $L^1$ and $M^1$ are as defined above; in the presence of a transition metal catalyst; or (C) reacting a compound of formula X with a compound of formula XI:

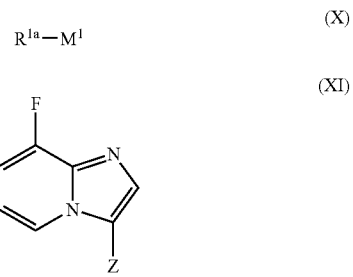

(X)

(XI)

wherein Z is as defined in claim 1, $M^1$ is as defined above, $R^{1a}$ represents an aryl or heteroaryl moiety, and $L^2$ represents a suitable leaving group; in the presence of a transition metal catalyst; or (D) reacting a compound of formula IV as defined above with a compound of formula VII:

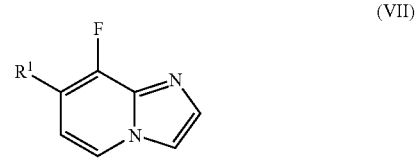

(VII)

wherein $R^1$ is as defined in claim 1; in the presence of a transition metal catalyst; and (E) subsequently, if required, converting a compound of formula I initially obtained into a further compound of formula I by standard methods.

* * * * *